(12) United States Patent
Guimberteau et al.

(10) Patent No.: US 8,821,935 B2
(45) Date of Patent: *Sep. 2, 2014

(54) MICROCAPSULES WITH MODIFIED RELEASE OF ACTIVE PRINCIPLES WITH LOW SOLUBILITY FOR ORAL DELIVERY

(75) Inventors: Florence Guimberteau, Montussan (FR); Catherine Castan, Orlienas (FR); Rémi Meyruiex, Lyons (FR); Gérard Soula, Meyzieu (FR)

(73) Assignee: Flamel Technologies, Venissieux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/583,940

(22) Filed: Oct. 20, 2006

(65) Prior Publication Data

US 2007/0160678 A1    Jul. 12, 2007

Related U.S. Application Data

(63) Continuation of application No. 11/358,047, filed on Feb. 22, 2006, now abandoned, which is a continuation of application No. 10/522,234, filed as application No. PCT/FR03/02384 on Jul. 28, 2003, now abandoned.

(51) Int. Cl.
  *A61K 9/14* (2006.01)
  *A61K 9/16* (2006.01)
  *A61K 9/50* (2006.01)

(52) U.S. Cl.
  CPC ............ *A61K 9/5015* (2013.01); *A61K 9/5026* (2013.01); *A61K 9/5047* (2013.01)
  USPC ........... 424/489; 424/498; 424/490; 424/494; 424/497

(58) Field of Classification Search
  None
  See application file for complete search history.

(56) References Cited

U.S. PATENT DOCUMENTS

| | | | |
|---|---|---|---|
| 4,321,253 A | 3/1982 | Beatty | |
| 4,748,023 A | 5/1988 | Tamas et al. | |
| 4,968,505 A | 11/1990 | Okada et al. | |
| 5,084,278 A * | 1/1992 | Mehta | 424/441 |
| 5,188,841 A | 2/1993 | Simpkin et al. | |
| 6,022,562 A * | 2/2000 | Autant et al. | 424/489 |
| 6,024,982 A | 2/2000 | Oshlack et al. | |
| 6,946,146 B2 * | 9/2005 | Mulye | 424/479 |
| 2013/0171223 A1* | 7/2013 | Zhou et al. | 424/401 |

FOREIGN PATENT DOCUMENTS

| | | |
|---|---|---|
| EP | 0207041 | 12/1986 |
| EP | 0 249 587 | 12/1987 |
| EP | 0709087 | 5/1996 |
| EP | 0 953 359 | 11/1999 |
| FR | 2313915 | 1/1977 |
| FR | 2670112 | 6/1992 |
| FR | 2 816 840 | 5/2002 |
| GB | 2 202 143 | 9/1988 |
| JP | 62240618 | 10/1987 |
| JP | 7252140 | 10/1995 |
| JP | 08073345 | 3/1996 |
| JP | 10509427 | 9/1998 |
| WO | WO-9611675 | 4/1996 |
| WO | WO-99/17752 | 4/1999 |
| WO | WO-9949846 | 10/1999 |
| WO | WO-0018374 | 4/2000 |
| WO | WO-00/38686 | 7/2000 |
| WO | WO-02/39984 | 5/2002 |
| WO | WO-02/094285 | 11/2002 |

OTHER PUBLICATIONS

Dubernet, C. and Benoit, J.P., La microencapsulation: ses techniques et ses applications en biologie, L'actualite chimique, pp. 19-28, Dec. 1986.

* cited by examiner

*Primary Examiner* — Michael G Hartley
*Assistant Examiner* — Nabila Ebrahim
(74) *Attorney, Agent, or Firm* — Squire Patton Boggs (US) LLP

(57) ABSTRACT

The present invention is directed to microcapsules for reliably modified release and adapted to industrial reproduction of an active principle hardly water-soluble, other than anti-hyperglycemia agents. Each of said microcapsules comprises a core of hardly soluble active principle and a coating film applied on the core. Their mean diameter is less than 1000 microns. The coating film contains a film-forming polymer (PI) insoluble in gastrointestinal tract fluids, a water-soluble polymer (P2), a plasticizer (PL), and optionally a lubricating surfactant (TA). Said coating film represents at least 4% p/p of dry matter of their total weight, and its components P1, P2, PL satisfy the following characteristics: dry weight mass fraction of PI relative to the total coating weight ranging between 40 and 90%; dry matter weight fraction of PL/P1+P2 ranging between 15 and 60%; dry matter weight fraction of PL/P1+P2 ranging between 1 and 30%. The present invention is also directed to the uses of said microcapsules in galenic formulation.

15 Claims, 1 Drawing Sheet

MICROCAPSULES WITH MODIFIED RELEASE OF ACTIVE PRINCIPLES WITH LOW SOLUBILITY FOR ORAL DELIVERY

CROSS-REFERENCE TO RELATED APPLICATIONS

This application claims priority to U.S. Ser. No. 11/358,047, filed Feb. 22, 2006, still pending, which is a continuation of U.S. Ser. No. 10/522,234, filed Jun. 9, 2006, abandoned, which is a national stage application of PCT/FR03/002384, filed Jul. 28, 2003, which claims priority to FR 02/09530, filed Jul. 26, 2002. The contents of which are incorporated herein in their entirety.

The field of the present invention is that of systems with modified release of medicinal and/or nutritional active principles (APs), intended to be administered orally.

The present invention also relates to microcapsules intended to be administered per os and containing at least one AP with low solubility.

The invention also relates to the medicinal products containing these microcapsules mentioned above and to the use of the latter for producing medicinal products.

In the present disclosure, the expression "modified release" denotes without distinction a release of the active principle(s) beginning as soon as the pharmaceutical form has been brought into contact with its dissolving medium (in vivo or in vitro) or else a release of the active principle(s) beginning only after a predetermined period of time ranging, for example, from 0.5 to several hours. Thus, for the purpose of the invention, a prolonging of the release corresponds to a release time for 50% of the active principle(s) which is typically several hours and which can extend from 0.25 to 20 hours, for example.

The expression "low solubility" relates to active principles the water-solubility of which is less than 10 g/l at 25° C.

More precisely, the invention relates to pharmaceutical formulations with prolonged release of active principles with low solubility, this formulation consisting of a plurality of microcapsules consisting of a core containing the active principle of low solubility and coated with a layer of polymer which controls the release of the AP.

Among the various modified-release systems, pharmaceutical systems with modified release consisting of a plurality of microcapsules of the reservoir type with an average diameter of less than 1000 microns are particularly advantageous. In fact, in these systems, the dose of active principle(s) to be administered is distributed among a large number of microcapsules (typically 10 000 for a dose of 500 mg and a diameter of 400 microns) and this type of system, as a result, has the following intrinsic advantages:

- the use of a mixture of microcapsules having different modified-release profiles makes it possible to produce release profiles exhibiting several waves of release or providing, by means of appropriate regulation of the various fractions, a constant plasma concentration level of the AP;
- the sensitivity to the variability of gastric emptying is lower, since the emptying, which takes place here with respect to a large number of particles, is statistically more reproducible;
- contact of the tissues with a high dose of AP, "dose dumping", is avoided. Each microcapsule in fact contains only a very low dose of active principle (s). The risk of tissue deterioration through local overconcentration of aggressive active principle(s) is thus avoided;
- it is possible to combine several pharmaceutical forms (immediate and/or delayed and/or prolonged release) comprising one or more active principles, in these "multimicrocapsular" systems;
- it does not induce any degradation of the AP;
- the amount of time spent by the microcapsules in the upper parts of the tract can be prolonged, which ensures an increase in the amount of time spent by the active principle(s) in passing in front of the absorption windows and thus maximizes the bioavailability of the active principle(s).

However, when the solubility of the AP is low, the production of a microparticulate modified-release form comes up against a substantial difficulty.

The diffusion of the active principle through the coating film surrounding each microcapsule takes place under the action of the dissolved AP concentration gradient between the inside and the outside of the microcapsule. In other words, it is the difference in osmotic pressure of the AP between the inside and the outside of the microcapsule which drives the release. The internal concentration of AP is the saturation concentration. The external concentration of AP is, for its part, negligible under usual conditions (termed "sink"). The driving of release is therefore directly linked to the saturation concentration of the AP, i.e. to its solubility.

For APs with low solubility, the saturation concentration of AP is relatively low and the diffusion of the AP to the outside is therefore, a priori, very slow, even for coating films that are not very thick.

Furthermore, in any case, for thin coating films, the following difficulties are then encountered:

(a) The depositing of a very thin coating film is not even: there are gaps next to areas that are too thick, and the release of the AP is not prolonged.

(b) The industrial control of the process for a very thin deposit becomes very difficult and relatively unreproducible.

Moreover, for thicker coating films, the release of the AP is extremely slow, or even nonexistent.

This technical problem is all the more difficult to solve in that it must not be down to the detriment of the other specifications required for a pharmaceutical system for oral administration of AP, which are, inter alia, cumulatively and for a wide range of APs, as follows:

- slow transit in the upper parts of the gastrointestinal tract, reflected by an in vivo absorption profile which is over a period of time notably longer than that permitted by the natural transit (3 h+/−1),
- absence of irritation of the mucosa,
- limited mass of the pharmaceutical form corresponding to a dose,
- low cost price.

The difficulty in modifying the release of an AP with low solubility explains the small number of technical solutions which have been proposed to date.

As regards the solid, multimicrocapsular pharmaceutical systems, those consisting of a multiplicity of particles or microcapsules each carrying active principle(s) coated with a film-coating layer based on ethylcellulose, on polyvinylpyrrolidone, on magnesium stearate and on castor oil, for example, are known. Such a pharmaceutical system is disclosed in PCT application WO 96/11675. These microcapsule reservoirs obtain an advantage from their multiplicity, which is a more even and reproducible gastric emptying time. In addition, their size is between 50 and 1000 μm and also the characteristics of their coating make it possible to increase their transit time in the upper parts of the gastrointestinal tract and, consequently, to maintain absorption of the active principle(s) for all or part of this time spent in the small intestine.

However, the multimicrocapsular pharmaceutical system according to WO 96/11675 is perfectable as regards APs with low solubility that can be administered orally, since it does not propose any solution to the problem of the diffusion of such an AP with low solubility through a coating film of sufficiently large thickness, for example of several microns.

In the field of microcapsules with modified release of blood glucose-lowering active principles, mention should be made of French patent application FR-A-2 816 840 which discloses microcapsules in which the core consists of metformin crystals coated with a membrane for controlling the release of the metformin, comprising stearic acid (50%) or castor oil (10%) and ethylcellulose (respectively 50 and 90%). This pharmaceutical system, for the oral administration of blood glucose-lowering active principles, should make it possible to obtain an effective therapeutic coverage over 24 hours by overcoming the problems of by-pass of the absorption window and of massive localized release of active principle.

This technical problem remains perfectible, insofar as it does not solve the problem of the low-solubility APs mentioned above.

As regards the prior art on microcapsules with modified release of active principles with low solubility, mention should first of all be made of PCT patent application WO 99/49846 which describes a pharmaceutical preparation composed of submicronic (0.05 to 10 µm) particles combining an active principle with low solubility with a phospholipid compound, a surface charge-modifying compound and a block polymer. The aim of this preparation is to improve the bioavailability and the stability of the active principle and it finds its applications in injectable forms or alternatively in forms intended to be administered ocularly or nasally. A prolonged-release form is only obtained in the case of intramuscular injection.

PCT patent application WO 00/18374 describes an invention of the same type as the previous one: the active principle in the form of submicronic (<1000 nm) particles is stabilized by a compound associated at the surface of the particles and mixed with a polymer. This mixture can then be formulated into granules or pellets and, optionally, into tablets. The active principle is rapidly dissolved and it is the increase in bioavailability obtained by virtue of the decrease in size which makes it possible to have an effective plasma concentration over a prolonged period.

Patent application GB-2 202 143 describes spheroids of diameter greater than 0.5 mm, and preferably greater than 0.8 mm, containing the poorly soluble active principle dispersed in 70 to 99.5% of microcrystalline cellulose. This matricial form requires no coating controlling the release of the active principle.

Patent application. JP-8073345 describes a controlled-release system composed of a film-coated granule. The granule contains an active principle with low solubility at neutral pH and inorganic acids. This system therefore proposes a solution that is only suitable for the case of basic active principles with low solubility.

Finally, European patent EP-B-0 249 587 concerns a solid preparation for the slow release of an active substance with low solubility (<0.1% by weight). This controlled-release preparation can be provided in the form of gelatin capsules comprising capsules consisting of coated granules. The granules comprise the active principle with low solubility and a solubilizing agent consisting of the commercial product Cremophor® RH 40 (polyoxyethylenated hydrogenated castor oil: 40 ethylene oxide units), and also other additives such as polyvinylpyrrolidone, cellulose, starch and lactose. These granules of size of between 700 and 1120 µm are covered with an ethylcellulose coating layer for controlling release. The ingredients of the granules, namely polyvinylpyrrolidone, cellulose, cornstarch and lactose, appear to be the elements of the hydrophilic gel system specific to the pharmaceutical form according to EP-B-0 24.9 587. These capsules therefore comprise a single constituent (ethylcellulose) in their coating layer, which limits its capacities in terms of modification of the release of the active principle. In particular, it is doubtful whether a coating layer composed only of ethylcellulose (known to form impermeable films) would allow the release of an AP with low solubility in a controlled and industrially reproducible manner over a period of several hours, for example.

None of these patent applications describes microparticles of the reservoir type or microcapsules for which the prolonged release of the active principle with low solubility is controlled by means of its diffusion through a membrane that is sufficiently thick to ensure a controlled and industrially reproducible permeability. Neither do they teach the manner in which such a system can be successfully achieved.

In the face of this vacuity of the prior art, one of the essential objectives of the present invention is to propose a form with modified release of AP(s) with low solubility consisting of a plurality of microcapsules, each formed by a core containing the AP and coated with a coating film.

Another objective of the present invention is to provide a plurality of reservoir-type microcapsules of AP of low solubility, for oral administration of the latter, the coating film of these microcapsules being sufficiently thick to ensure a controlled and industrially reproducible permeability.

Another essential objective of the present invention is to provide a plurality of microcapsules of AP(s) with low solubility, less than 1000 µm in size.

Another objective of the present invention is to propose an oral pharmaceutical form consisting of a large number (for example of the order of several thousand) of microcapsules, this multiplicity ensuring, statistically, good reproducibility of the kinetics of transit of the AP in the entire gastrointestinal tract, such that better control of the bioavailability and therefore better effectiveness result therefrom.

Another essential objective of the present invention is to provide a plurality of microcapsules of AP(s) with low solubility, for oral administration of the latter according to a prolonged and/or optionally delayed release profile, such that the half-release time, $t_{1/2}$, is between 0.25 and 20 hours.

Another essential objective of the present invention is to provide an oral form with modified release in which the AP(s) is (are) in the form of a plurality of particles individually coated to form microcapsules, and in which it is possible to mix several active principles in multimicrocapsular form, that are released according to different respective release times.

Having set themselves all the above objectives among others, the inventors have, to their credit, developed a multimicrocapsular pharmaceutical system with prolonged release of AP(s) with low solubility, by oral administration, which, besides the properties targeted in the aims above, has, cumulatively and for a wide range of APs, the following specifications, inter alia:

absence of irritation of the mucosa,
high AP content,
low cost price,
which makes it possible to adjust the AP half-release time to between 0.25 and 20 hours,
which is reproducible and easy to implement industrially by virtue of a ratio of the mass of the coating film to the mass of the particle of greater than 3% dry weight/dry weight, preferably greater than 5% dry weight/dry weight, and even more preferably of between 3 and 40% dry weight/dry weight.

To do this, the inventors have, to their credit, discovered, after many trials, microcapsules with a particular structure which maker it possible to satisfy the objectives recalled above, among others.

To this end, a subject of the present invention a pharmaceutical system made up of microcapsules for the modified release of at least one AP with low water solubility, with the possible exclusion of blood glucose-lowering agents, intended to be administered orally and of the type of those:
  each consisting of a core comprising at least one active principle and of a coating film applied onto the core and controlling the prolonged release of the AP(s),
  the mean diameter of which is less than 1000 microns, preferably between 800 and 50 microns, and even more preferably between 600 and 100 microns,
  in which the coating film of each microcapsule contains the following components:
    -I—at least one film-forming polymer (P1) insoluble in gastrointestinal tract fluids,
    -II—at least one water-soluble polymer (P2)
    -III—at least one plasticizer (PL),
    -IV—and, optionally, at least one lubricating surfactant (TA);
with the possible exclusion of coating films consisting of enteric compositions and of coating films having the composition below:
1—at least one film-forming polymer (P1) insoluble in the fluids of the tract, present in a proportion of 50 to 90, preferably 50 to 80% by weight on a dry basis relative to the total mass of the coating composition and consisting of at least one water-insoluble derivative of cellulose, i.e. ethylcellulose and/or cellulose acetate;
2—at least one nitrogenous polymer (P2) present in a proportion of 2 to 25, preferably 5 to 15% by weight on a dry basis relative to the total mass of the coating composition and consisting of at least one polyacrylamide and/or one poly-N-vinyl-amide and/or one poly-(N-vinyl lactam), i.e. polyacrylamide and/or polyvinylpyrrolidone;
3—at least one plasticizer present in a proportion of 2 to 20, preferably 4 to 15% by weight on a dry basis relative to the total mass of the coating composition and consisting of at least one of the following compounds: glyceryl esters, phthalates, citrates, sebacates, cetyl alcohol esters, castor oil, salicylic acid and cutin;
4—and at least one surfactant and/or lubricant, present in a proportion of 2 to 20, preferably 4 to 15% by weight on a dry basis relative to the total mass of the coating composition and chosen from anionic surfactants, i.e. alkali metal salts or alkaline-earth metal salts of fatty acids, stearic acid and/or oleic acid being preferred, and/or from nonionic surfactants, i.e. polyoxy-ethylenated sorbitan esters and/or polyoxy-ethylenated castor oil derivatives, and/or from lubricants such as calcium stearate, magnesium stearate, aluminum stearate or zinc stearate, or such as sodium stearyl fumarate and/or glyceryl behenate; it being possible for said agent to comprise just one or a mixture of the abovementioned products;
characterized:
  in that their coating film represents at least 3% dry weight/dry weight, preferably at least 5% dry weight/dry weight of their total mass,
  and in that the components P1, P2 and PL of the coating film satisfy the following characteristics:
    mass fraction by dry weight of P1 relative to the total mass of the coating of between 40 and 90%, and preferably of between 50 and 80%;
    mass fraction by dry weight P2/P1+P2 of between 15 and 60%, and preferably of between 15 and 55%;
    mass fraction by dry weight PL/P1+PL of between 1 and 30%, and preferably of between 5 and 25%.

To the applicant's credit, it has developed, entirely surprisingly and unexpectedly, such a pharmaceutical system that allows diffusion of the AP with low solubility through a sufficiently thick coating film for the microcapsules, and without putting a strain on the cost price.

The choice of an amount of coating greater than or equal to 3% by weight on a dry basis relative to the total mass of the microcapsule is a particularly inventive provision which goes against the technical opinion commonly held in this field. The same is true as regards the quantitative data for P1, P2 and PL.

According to a particularly preferred embodiment of the invention, the coating film represents 3 to 40% w/w on a dry basis of the total mass of the microcapsules.

Preferably, P1 is selected from the group of products below:
  water-insoluble derivatives of cellulose, preferably ethylcellulose and/or cellulose acetate,
  acrylic derivatives,
  poly(vinyl acetates),
  and mixtures thereof.

Preferably, P2 is selected from the group of products below:
  water-soluble derivatives of cellulose,
  polyacrylamides,
  poly-N-vinylamides,
  poly(N-vinyl lactams),
  polyvinyl alcohols (PVAs),
  polyoxyethylenes (POEs),
  polyvinylpyrrolidones (PVPs) (the latter being preferred),
  and mixtures thereof.

Preferably, PL is selected from the group of products below:
  glycerol and esters thereof, preferably from the following subgroup:
    acetylated glycerides, glyceryl mono-stearate, glyceryl triacetate, glyceryl tributyrate,
  phthalates, preferably from the following subgroup:
    dibutyl phthalate, diethyl phthalate, dimethyl phthalate, dioctyl phthalate,
  citrates, preferably from the following subgroup:
    acetyl tributyl citrate, acetyl triethyl citrate, tributyl citrate, triethyl citrate,
  sebacates, preferably from the following subgroup:
    diethyl sebacate, dibutyl sebacate,
  adipates,
  azelates,
  benzoates,
  plant oils,
  fumarates, preferably diethyl fumarate,
  malates, preferably diethyl malate,
  oxalates, preferably diethyl oxalate,
  succinates, preferably dibutyl succinate,
  butyrates,
  cetyl alcohol esters,
  salicylic acid,
  triacetin,
  malonates, preferably diethyl malonate,
  cutin,
  castor oil (this being particularly preferred),
  and mixtures thereof.

According to an advantageous variant, the coating film comprises component TA in a proportion of 2 and 20%, and preferably of between 4 and 15% of the total mass of the dry coating.

Preferably, TA is selected from the group of products below:
- anionic surfactants, preferably from the subgroup of alkali metal salts or alkaline-earth metal salts of fatty acids, stearic acid and/or oleic acid being preferred,
- and/or nonionic surfactants, preferably from the following subgroup:
  - polyoxyethylenated oils, preferably polyoxyethylenated hydrogenated castor oil,
  - polyoxyethylene-polyoxypropylene copolymers,
  - polyoxyethylenated sorbitan esters,
  - polyoxyethylenated castor oil derivatives,
  - stearates, preferably calcium stearate, magnesium stearate, aluminum stearate or zinc stearate,
  - stearyl fumarates, preferably sodium stearyl fumarate,
  - glyceryl behenate,
  - and mixtures thereof.

Advantageously, the microcapsules are designed so as to be able to spend at least approximately 5 hours, preferably at least approximately 8 hours, in the upper parts of the gastrointestinal tract, and thus allow absorption of the AP for a prolonged period of time.

According to a particular embodiment of the microcapsules containing APs with low solubility according to the invention, and according to another quantitative mode of expression, the coating film comprises from 35 to 75% of ethylcellulose P1, from 20 to 50% of polyvinylpyrrolidone P2, from 5 to 15% of PL.

This preparation according to the invention makes it possible to produce a multimicrocapsular form with modified release of APs with low solubility, it being possible for the AP half-release time to be adjusted to between 0.25 and 20 hours in a reproducible manner through the use of a coating film, that can be described as a diffusion coating film, which is sufficiently thick.

Moreover, for APs with low solubility for which the absorption window is limited, such a plurality of microcapsules (typically 10 000 for a dose of 500 mg and a mean diameter of 400 microns) has the following intrinsic advantages:
- The use of a mixture of microcapsules having different delayed- and controlled-release profiles makes it possible to produce release profiles exhibiting several waves of release or providing, by means of adequate regulation of the various fractions, a constant plasma concentration level of the AP.
- The variability of gastric emptying is lower, since the emptying, which takes place here with respect to a large number of particles, is statistically more reproducible.
- Contact of the tissues with a high dose of AP, "dose dumping", is avoided. Each microcapsule in fact contains only a very low dose of AP. The risk of tissue deterioration through a local overconcentration of aggressive AP is thus avoided.
- The amount of time spent by the microcapsules in the upper parts of the tract can be prolonged, which ensures an increase in the amount of time spent by the AP in passing in front of the absorption windows and thus maximizes the bioavailability of the AP.

The APs with low solubility used for preparing the modified-release, preferably controlled release, microcapsules according to the invention can be chosen from at least one of the major varieties of active substances below: antiulcer agents, antidiabetic agents, anticoagulants, antithrombics, blood lipid-lowering agents, anti-arrhythmics, vasodilators, antiangina agents, anti-hypertensives, vasoprotective agents, fertility promoters, inducers and inhibitors of uterine labor, contraceptives, antibiotics, antifungal agents, anti-viral agents, anticancer, agents, anti-inflammatories, analgesics, antiepileptics, antiparkinsonian agents, neuroleptics, hypnotics, anxiolytics, psychostimulants, antimigraine agents, antidepressives, antitussives, antihistamines or antiallergic agents.

Preferably, the AP(s) is (are) chosen from the following compounds: prazosine, acyclovir, nifedipine, naproxen, ibuprofen, ketoprofen, fenoprofen, indomethacine, diclofenac, sulpiride, terfenadine, carbamazepine, fluoxetine, alprazolam, famotidine, ganciclovir, spironolactone, acetylsalicylic acid, quinidine, morphine, amoxicillin, paracetamol, metoclopramide, verapamil and mixtures thereof.

According to one variant, the AP consists of at least one nutritional and/or dietetic supplement, preferably chosen from vitamins, amino acids, trace elements, antioxidants and mixtures thereof.

As regards the preparation of the microcapsules according to the invention, this goes back to micro-encapsulation techniques accessible to those skilled in the art, the principles of which are summarized in the article by C. Duverney and J. P. Benoit in "L'actualite chimique" [Current use in chemistry], December 1986. More precisely, the technique under consideration is microencapsulation by film-coating, resulting in individualized "reservoir" systems as opposed to matricial systems.

For further details, reference will be made to patent EP-B-0.953 359.

The AP particles of desired mean particle size necessary for preparing the microcapsules according to the invention may be crystals of pure AP and/or AP that has undergone a pretreatment by one of the conventional techniques in the field, such as for example granulation, in the presence of at least one conventional binding agent and/or of an agent for modifying the intrinsic solubility characteristics of the AP.

The present invention is also directed toward a medicinal product comprising the microcapsules as defined above.

This medicinal product may be in solid form: tablet, gelatin capsule, powder, etc, or a in liquid form, for example an aqueous suspension.

In accordance with the invention, it is also proposed, as a solution to the problems mentioned at the beginning of the present disclosure, namely: modified, preferably prolonged, release of APs with low solubility, in a pharmaceutical form that can be readily swallowed, all this in a perspective of long, effective and safe therapeutic coverage,
to use a plurality of microcapsules for the modified release of at least one AP with low water solubility, with the possible exclusion: of blood glucose-lowering agents, intended to be administered orally, these microcapsules having these following characteristics:
- they each consist of a core comprising at least one active principle and of a coating film applied onto the core and controlling the prolonged release of the AP(s),
- their mean diameter is less than 1000 microns, preferably between 800 and 50 microns, and even more preferably between 600 and 100 microns,
- their coating film contains the following components:
  - -I—at least one film-forming polymer (P1) insoluble in gastrointestinal tract fluids,
  - -II—at least one water-soluble polymer (P2),
  - -III—at least one plasticizer (PL), -IV—and, optionally, at least one lubricating surfactant (TA);

components P1, P2 and PL of the coating film satisfying the following characteristics:

mass fraction by dry weight of P1 relative to the total mass of the coating of between 40 and 90%, preferably of between 50 and 80%;

mass fraction by dry weight of P2/P1+P2 of between 15 and 60%, and preferably of between 15 and 55%;

mass fraction by dry weight PL/P1+PL of between 1 and 30%, and preferably of between 5 and 25%, and this coating film represents at least 3% dry weight/dry weight, preferably at least 5% dry weight/dry weight of their total mass;

with the possible exclusion of coating films consisting of enteric compositions and of coating films having the composition below:

1—at least one film-forming-polymer (P1) insoluble in the fluids of the tract, present in a proportion of 50 to 90, preferably 50 to 80% by weight on a dry basis relative to the total mass of the coating composition and consisting of at least one water-insoluble derivative of cellulose, i.e. ethylcellulose and/or cellulose acetate;

2—at least one nitrogenous polymer (P2) present in a proportion of 2 to 25, preferably 5 to 15% by weight on a dry basis relative to the total mass of the coating composition and consisting of at least one polyacrylamide and/or one poly-N-vinyl-amide and/or one poly(N-vinyl lactam), i.e. polyacrylamide and/or polyvinylpyrrolidone;

3—at least one plasticizer present in a proportion of 2 to 20, preferably 4 to 15% by weight on a dry basis relative to the total mass of the coating composition and consisting of at least one of the following compounds: glyceryl esters, phthalates, citrates, sebacates, cetyl alcohol esters, castor oil, salicylic acid and cutin;

4—and at least one surfactant and/or lubricant, present in a proportion of 2 to 20, preferably 4 to 15% by weight on a dry basis relative to the total mass of the coating composition and chosen from anionic surfactants, i.e. alkali metal salts or alkaline-earth metal salts of fatty acids, stearic acid and/or oleic acid being preferred, and/or from nonionic surfactants, i.e. polyoxy-ethylenated sorbitan esters and/or polyoxy-ethylenated castor oil derivatives, and/or from lubricants such as calcium stearate, magnesium stearate, aluminum stearate or zinc stearate, or such as sodium stearyl fumarate and/or glyceryl behenate; it being possible for said agent to comprise just one or a mixture of the abovementioned products;

for producing a medicinal product based on at least one AP with low solubility which can be administered orally, which can be readily swallowed, and which is released in vivo in a controlled, prolonged and, optionally, delayed manner.

According to yet another of its objects, the present invention relates to a method of therapeutic treatment, in which use is made of a medicinal product as defined above as a product per se or as a product obtained by means of the method described above.

The invention will be understood more fully, in terms of its composition and the properties and obtaining thereof, on reading the examples below, given only by way of illustration and making it possible to highlight the variants of implementation and the advantages of the invention.

EXAMPLES

Example 1

Preparation of Acyclovir Microcapsules

Step 1: Granule 970 g of Acyclovir and 30 g of Povidone (Plasdone® K29/32) are dry-mixed beforehand in the tank of a high-shear granulator (Lodige® M5MRK) for 5 minutes. This pulverulent mixture is then granulated with water (200 g). The granules are dried at 40° C. in a ventilated oven, and then sized on a 500 µm screen. The 200-500 µm fraction is selected by sieving.

Step 2: Coating 700 g of granules obtained above are coated, in a Glatt® GPCG1 fluidized airbed device, with 50.65 g of ethylcellulose (Ethocel® 7 Premium), 50.65 g of Povidone (Plasdone® K29/32), 12.35 g of magnesium stearate and 9.88 g of castor oil dissolved in an acetone/isopropanol (60/40 m/m) mixture.

| Microcapsule composition: | | |
|---|---|---|
| Ingredients | % by mass | Production formula (in g) |
| Acyclovir granules | 85.0 | 700.0 L |
| Plasdone ® K29/32 | (2.55) | |
| Acyclovir | (82.45) | |
| Coating | 15.0 | 123.5 |
| Ethocel ® 7 Premium | (6.15) | |
| Plasdone ® K29/32 | (6.15) | |
| magnesium stearate | (1.50) | |
| castor oil | (1.20) | |

Test:

The kinetics of release of the Acyclovir are determined by means of a dissolving test (type II device according to the European pharmacopoeia, 3rd edition, phosphate buffer medium, pH 6.8, volume 900 ml, temperature 37° C., 100 rpm paddle agitation, UV detection at 268 nm).

Figure 1:
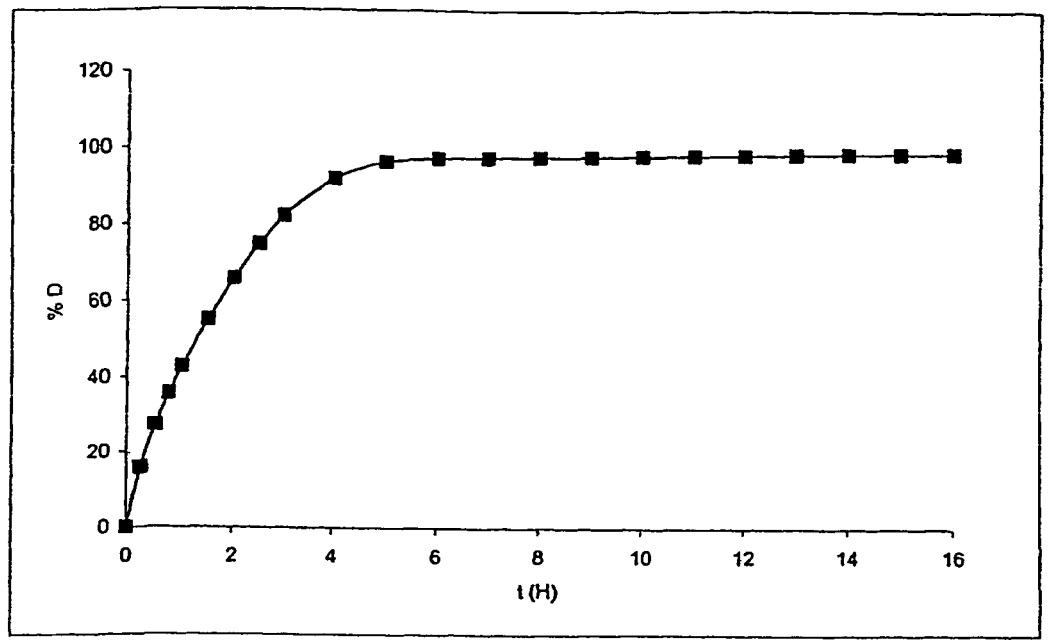
FIG. 1 represents the curve of the percentage dissolution (% D) of the active principle AP, as a function of the time (t) in hours (H), of the microcapsules of example 1, in the dissolving test described in the following examples.

Result:

The attached FIG. 1 shows the dissolution profile obtained by means of these microcapsules.

The microcapsule composition described above makes it possible to obtain a dissolution profile characterized by 80% of Acyclovir released at 3 hours.

Example 2

Preparation of Amoxicillin Microcapsules

Step 1: Granule 970 g of amoxicillin trihydrate and 30 g of Povidone (Plasdone® K29/32) are dry-mixed beforehand in the tank of a high-shear granulator (Lodige® M5MRK) for 5 minutes. This pulverulent mixture is then granulated with water (200 g). The granules are dried at 40° C. in a ventilated oven and then sized on a 500 µm screen. The 200-500 µm fraction is selected by sieving.

Step 2: Coating 700 g of granules obtained above are coated, in a Glatt® GPCG1 fluidized airbed device, with g of ethylcellulose (Ethocel® 7 Premium), g of Povidone (Plasdone® K29/32) and 0.96 g of castor oil dissolved in an acetone/isopropanol (60/40 m/m) mixture.

Microcapsule composition

| Ingredients | % by mass | Production formula (in g) |
|---|---|---|
| Amoxicillin granules | 82.0 | 700.0 |
| Plasdone ® K29/32 | (0.45) | |
| Amoxicillin trihydrate | (14.55) | |
| Coating | 18.0 | 153.6 |
| Ethocel ® 7 Premium | (12.60) | |
| Plasdone ® K29/32 | (4.14) | |
| Castor oil | (1.26) | |

Test:

The kinetics of release of the amoxicillin are determined by means of a dissolving test (type II device according to the European pharmacopoeia, 3rd edition, phosphate buffer medium, pH 6.8, volume 900 ml, temperature 37° C., 100 rpm paddle agitation, UV detection at 240 nm).

Figure 2:
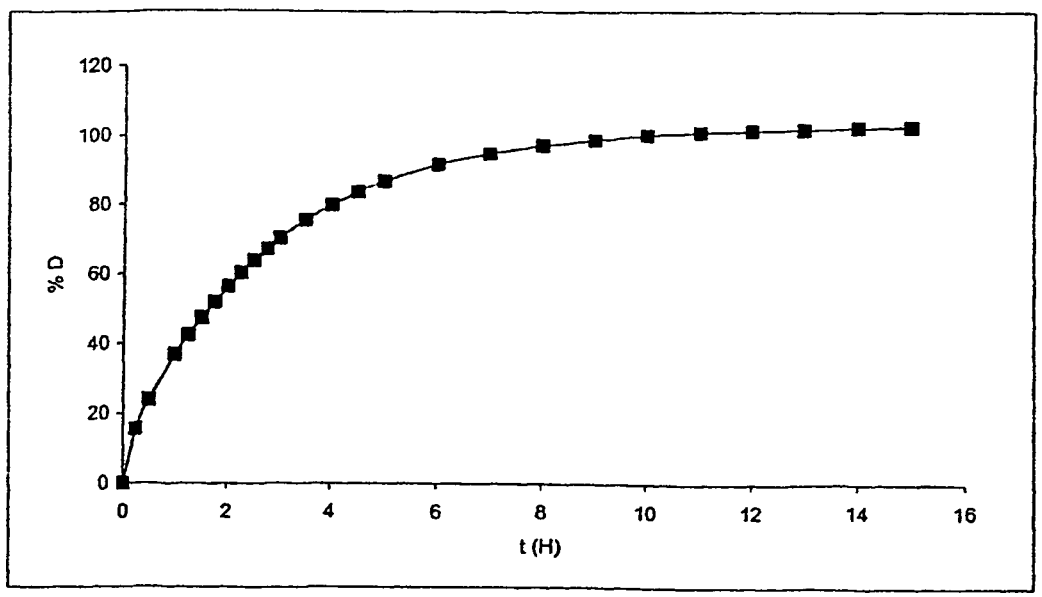
FIG. 2 represents the curve of the percentage dissolution (% D) of the active principle AP, as a function of the time (t) in hours (H), of the microcapsules of example 2, in the dissolving test described in the following examples.

Result:

The attached FIG. 2 shows the dissolution profile obtained for these microcapsules.

The microcapsule composition described above makes it possible to obtain a dissolution profile characterized by 80% of amoxicillin released at 4 hours.

The invention claimed is:

1. A microcapsule for the modified release of at least one active principle with low water solubility,
    wherein the microcapsule comprises a core comprising at least one active principle, wherein at least one of the at least one active principle has low solubility, and a coating film applied onto the core, wherein the mean diameter of the microcapsule is less than 1000 microns,
    wherein the coating film is at least 3% dry weight to total weight, and comprises:
    I. at least one film-forming polymer selected from the group consisting of: acrylic derivatives, poly (vinyl acetate), water-insoluble derivatives of cellulose, and mixtures thereof, wherein the polymer is insoluble in gastrointestinal tract fluid;
    II. at least one water-soluble polymer selected from the group consisting of: water-soluble derivatives of cellulose, polyvinyl alcohols (PVAs), polyoxyethylenes (POEs), polyvinylpyrrolidones (PVPs), and mixtures thereof; and
    III. at least one plasticizer,
    wherein the at least one film-forming polymer insoluble in gastrointestinal tract fluid is between 50-80% dry weight relative to the total mass of the coating;
    wherein the mass fraction of the at least one water-soluble polymer dry weight, relative to the total dry weight of the at least one film-forming polymer insoluble in gastrointestinal tract fluids and of the at least one water-soluble polymer, is between 15 and 60%; and
    wherein the mass fraction of the at least one plasticizer dry weight, relative to the total dry weight of the at least one film-forming polymer insoluble in gastrointestinal tract fluids and the at least one plasticizer, is between 1 and 30%;
    wherein the coating film does not comprise the following combination of components:
    at least one film-forming polymer insoluble in gastrointestinal tract fluid, present in a proportion of 50 to 90% by weight on a dry basis relative to the total mass of the coating composition, and consisting of water-insoluble derivatives of cellulose;
    at least one nitrogenous polymer, present in a proportion of 2 to 25% by weight on a dry basis relative to the total mass of the coating composition, and consisting of; polyacrylamide, poly-N-vinyl-amide, poly-(N-vinyl-lactam), and mixtures thereof;
    at least one plasticizer, present in a proportion of 2 to 20% by weight on a dry basis relative to the total mass of the coating composition, and consisting of: glyceryl esters, phthalates, citrates, sebacates, cetyl alcohol esters, castor oil, salicylic acid, cutin, and mixtures thereof; and
    at least one surfactant or lubricant, present in a proportion of 2 to 20% by weight on a dry basis relative to the total mass of the coating composition, and consisting of: anionic surfactants, nonionic surfactants, lubricants, and mixtures thereof.

2. The microcapsule of claim 1, wherein the at least one plasticizer is selected from the group comprising: glycerol and esters thereof, acetylated glycerides, glyceryl monostearate, glyceryl triacetate, glyceryl tributyrate, phthalates, dibutyl phthalate, diethyl phthalate, dimethyl phthalate, dioctyl phthalate, citrates, acetyl tributyl citrate, acetyl triethyl citrate, tributyl citrate, triethyl citrate, sebacates, diethyl sebacate, dibutyl sebacate, adipates, azelates, benzoates, plant oils, fumarates, diethyl fumarate, malates, diethyl malate, oxalates, diethyl oxalate, succinates, dibutyl succinate, butyrates, acetyl alcohol esters, salicylic acid, malonates, diethyl malonate, castor oil, and mixtures thereof.

3. The microcapsule of claim 1, wherein the coating film also comprises
    IV. at least one lubricating surfactant.

4. The microcapsule of claim 3, wherein the at least one lubricating surfactant is in a proportion of 2 to 20% of the total mass of the dry coating.

5. The microcapsule of claim 3, wherein the at least one lubricating surfactant is selected from the group comprising: anionic surfactants, alkali metal salts of fatty acids, alkaline-earth metal salts of fatty acids, stearic acid, oleic acid, polyoxyethylene oils, polyoxyethylenated hydrogenated castor oil, polyoxyethylene-polyoxypropylene copolymers, polyoxyethylenated sorbitan esters, polyoxyethylenated castor oil derivatives, stearates, calcium stearate, magnesium stearate, aluminum stearate, zinc stearate, stearyl fumarates, sodium stearyl fumarate, glyceryl behenate, and mixtures thereof.

6. The microcapsule of claim 1, wherein the microcapsule mean diameter is between 800 and 50 microns.

7. The microcapsule of claim 6, wherein the microcapsule mean diameter is between 600 and 100 microns.

8. The microcapsule of claim 1, wherein the active principle is selected from the group comprising: antiulcer agents, antidiabetic agents, anticoagulants, antithrombics, blood lipid-lowering agents, antiarrhythmics, vasodilators, antiangina agents, antihypertensives, vasoprotective agents, fertility promoters, inducers and inhibitors of uterine labor, contraceptives, antibiotics, antifungal agents, antiviral agents, anticancer agents, anti-inflammatories, analgesics, antiepileptics, antiparkinsonian agents, neuroleptics, hypnotics, anxiolytics, psychostimulants, antimigraine agents, antidepressives, antitussives, antihistamines and antiallergic agents.

9. The microcapsule of claim 1, wherein the active principle is selected from the group comprising: prazosine, acyclovir, nifedipine, naproxen, ibuprofen, ketoprofen, fenoprofen, indomethacine, diclofenac, sulpiride, terfenadine, carbamazepine, fluoxetine, alprazolam, famotidine, ganciclovir, spironolactone, acetylsalicyclic acid, quinidine, morphine, amioxicillin, paracetamol, metoclopramide, verapamil and mixtures thereof.

10. A medicinal product comprising the microcapsules of claim 1.

11. The medicinal product of claim 10, wherein the form of the medicinal product is selected from the group comprising: tablet, gelatin capsule, powder, liquid, and an aqueous suspension.

12. A method of controlling the in vivo release of at least one active principle with a low water solubility by use of orally administered microcapsules, wherein the microcapsules comprise a core comprising at least one active principle, wherein at least one of the at least one active principle has low solubility, and a coating film applied onto the core, wherein the mean diameter of the microcapsule is less than 1000 microns, and wherein the coating film is at least 3% dry weight to total weight, and comprises
I. at least one film-forming polymer selected from the group consisting of: acrylic derivatives, poly (vinyl acetate), water-insoluble derivatives of cellulose, and mixtures thereof, wherein the polymer is insoluble in gastrointestinal tract fluid;
II. at least one water-soluble polymer selected from the group consisting of: water-soluble derivatives of cellulose, polyvinyl alcohols (PVAs), polyoxyethylenes (POEs), polyvinylpyrrolidones (PVPs), and mixtures thereof; and
III. at least one plasticizer,
wherein the at least one film-forming polymer insoluble in gastrointestinal tract fluid is between 50-80% dry weight relative to the total mass of the coating;
wherein the mass fraction of the at least one water-soluble polymer dry weight, relative to the total dry weight of the at least one film-forming polymer insoluble in gastrointestinal tract fluids and in the at least one water-soluble polymer, is between 15 and 60%; and
wherein the mass fraction of the at least one plasticizer dry weight, relative to the total dry weight of the at least one film-forming polymer insoluble in gastrointestinal tract fluids and the at least one plasticizer, is between 1 and 30%;
wherein the coating film does not comprise the following combination of components:
at least one film-forming polymer insoluble in gastrointestinal tract fluid, present in a proportion of 50 to 90% by weight on a dry basis relative to the total mass of the coating composition, and consisting of water-insoluble derivatives of cellulose;
at least one nitrogenous polymer, present in a proportion of 2 to 25% by weight on a dry basis relative to the total mass of the coating composition, and consisting of; polyacrylamide, poly-N-vinyl-amide, poly-(N-vinyl-lactam), and mixtures thereof;
at least one plasticizer, present in a proportion of 2 to 20% by weight on a dry basis relative to the total mass of the coating composition, and consisting of: glyceryl esters, phthalates, citrates, sebacates, cetyl alcohol esters, castor oil, salicylic acid, cutin, and mixtures thereof; and
at least one surfactant or lubricant, present in a proportion of 2 to 20% by weight on a dry basis relative to the total mass of the coating composition, and consisting of: anionic surfactants, nonionic surfactants, lubricants, and mixtures thereof.

13. The method of claim 12, wherein the coating film also comprises
at least one lubricating surfactant.

14. The microcapsule of claim 1, wherein the at least one active principle has a water solubility less than 10 g/l.

15. The microcapsule of claim 1, wherein the microcapsules provide a prolonged or delayed release profile such that the half-release time $t_{1/2}$ is between approximately 0.25 and approximately 20 hours.

* * * * *